(12) United States Patent
Choate et al.

(10) Patent No.: US 7,811,456 B2
(45) Date of Patent: Oct. 12, 2010

(54) SYSTEMS AND METHODS FOR COMBINING AND CONVERTING SOLID AND LIQUID ORGANIC WASTE MATERIALS INTO USEFUL PRODUCTS

(75) Inventors: Chris E. Choate, Discovery Bay, CA (US); James H. Lord, Los Gatos, CA (US)

(73) Assignee: Recology Inc., San Francisco, CA (US)

( * ) Notice: Subject to any disclaimer, the term of this patent is extended or adjusted under 35 U.S.C. 154(b) by 211 days.

(21) Appl. No.: 12/287,519

(22) Filed: Oct. 10, 2008

(65) Prior Publication Data

US 2009/0095673 A1 Apr. 16, 2009

Related U.S. Application Data

(60) Provisional application No. 60/998,815, filed on Oct. 11, 2007.

(51) Int. Cl.
*C02F 3/28* (2006.01)
*C02F 11/04* (2006.01)
(52) U.S. Cl. .................................... 210/603; 435/262.5
(58) Field of Classification Search ................. 210/603, 210/173; 435/262, 262.5
See application file for complete search history.

(56) References Cited

U.S. PATENT DOCUMENTS 5,348,871 A * 9/1994 Scott et al. ................... 435/165
5,377,917 A * 1/1995 Wiljan et al. ................... 241/14
6,379,505 B1 * 4/2002 Wiljan et al. ................. 162/261

FOREIGN PATENT DOCUMENTS

EP 172443 A1 * 2/1986
GB 2143811 A * 2/1985
JP 2004-313899 A * 11/2004

* cited by examiner

*Primary Examiner*—Fred Prince
(74) *Attorney, Agent, or Firm*—Gard & Kaslow LLP

(57) ABSTRACT

Systems and methods are provided for converting organic waste materials from a municipal waste stream to useful products, such as fuels. Through the use of a biomixer and a hydropulper, as well as through sorting and screening, the organic waste materials are progressively reduced in size and cleaned of contamination. The resulting uniform biomass is suitable for anaerobic digestion to produce biogas and a residual solid that is suitable for producing a high quality compost. A quantity of liquid organic waste material can be added to the biomixer, to the hydropulper and/or to the anaerobic digester. The quantity of liquid organic waste material can be obtained by separating the liquids from any containers and can be stored in a holding tank prior to being added to the biomixer, the hydropulper and/or the anaerobic digester.

35 Claims, 4 Drawing Sheets

SYSTEMS AND METHODS FOR COMBINING AND CONVERTING SOLID AND LIQUID ORGANIC WASTE MATERIALS INTO USEFUL PRODUCTS

CROSS-REFERENCE TO RELATED APPLICATIONS

This applications claims priority to U.S. Provisional Application No. 60/998,815 filed on Oct. 11, 2007 and entitled "Systems and Methods for Combining and Converting Solid and Liquid Organic Waste Materials into Useful Products." This application is related to U.S. application Ser. No. 11/821,854 filed on Jun. 25, 2007, pending, and entitled "Systems and Methods for Converting Organic Waste Materials into Useful Products," U.S. Pat. No. 7,015,028 issued on Mar. 21, 2006 and entitled "Process for Treatment of Organic Waste Materials," U.S. application Ser. No. 10/954,550 filed on Sep. 29, 2004, now abandoned, and entitled "Systems and Methods for Treatment of Organic Waste Materials," U.S. patent application Ser. No. 11/031,218, now U.S. Pat. No. 7,316,921, filed on Jan. 6, 2005 and entitled "Organic Waste Material Treatment System," U.S. patent application Ser. No. 11/385,098, pending, filed Mar. 20, 2006 and entitled "Systems and Processes for Treatment of Organic Waste Materials," U.S. patent application Ser. No. 11/492,258, pending, filed on Jul. 24, 2006 and entitled "Systems and Processes for Treatment of Organic Waste Materials with a Biomixer," U.S. patent application Ser. No. 11/584,680, pending, filed Oct. 19, 2006 and entitled "Biomechanical Device for Producing a Biomass," and U.S. patent application Ser. No. 11/343,515, abandoned, filed on Jan. 30, 2006 and entitled "Process for Generating Useful Biomass from Organic Waste Streams." Each of the above-referenced applications is incorporated herein by reference.

BACKGROUND OF THE INVENTION

1. Field of the Invention

The present invention relates generally to processing of waste materials, and more particularly to systems and processes for handling solid and liquid organic waste materials.

2. Description of the Prior Art

The traditional method of solid waste handling has been landfilling, the process of burying waste in a landfill. However, landfilling can cause environmentally unacceptable pollution discharges to the water and, as real estate values increase, is considered to be an unattractive use of land. Thus, current waste management strategies seek to limit the amount of refuse directed to landfills. Recycling and composting programs have become widely accepted for both commercial and residential waste to reduce the demands on landfills.

An alternative to composting for non-recyclable solid waste are refuse-to-energy plants where material is burned to create energy. Refuse-to-energy plants first process the waste by grinding and then burning the ground material. Although efforts are made to separate out hazardous materials from the waste stream, these plants have had a history of emissions and operational problems related to contaminants. The residual ash created from this burning has also, in some cases, been found to be hazardous.

Another type of organic waste material comprises the liquid discharge handled by sewage treatment plants. This material typically has high organic content in the form of biological or chemical oxygen demand (BOD & COD), and may have relatively high suspended solids (SS) content even though the material is classified as a liquid and will flow.

Anaerobic digestion presents an alternative for handling organic waste materials, both solids and liquids. The primary objective of anaerobic digestion is the production of a mixture of hydrocarbon gases ("biogas"), which may be utilized as an energy source to generate electricity and/or heat. Any solid material remaining at the completion of the anaerobic digestion process is typically disposed of by conventional landfilling or composted into a soil amendment.

Because of the high capital costs associated with anaerobic digestion equipment, and the environmental issues associated with refuse-to-energy plants, composting has become the dominant method in the United States for the management and re-use of organic waste materials generated in rural and suburban settings. The growing use of composting as a preferred alternative to disposal of organic waste material has also created some environmental problems. These problems include emissions of noxious gases and ozone pre-cursors, runoff from the compost facility, and high energy consumption during material processing. These problems may become particularly acute if the organic waste material contains large amounts of food waste or other high moisture content waste.

In the case of liquid organic waste produced by industry, this material is typically disposed of through municipal sewer systems. In some instances, because of the nature of the liquid organic waste, the producer may be required to perform certain pretreatment or complete treatment steps prior to discharging the liquid organic waste into the sewer system. In other cases, the producer is required to pay a surcharge to discharge the liquid organic waste into the sewer system. When discharged liquid organic waste reaches a sewage treatment plant, the liquid organic waste undergoes a number of processing steps before reaching the final treatment step of anaerobic digestion. Unfortunately, a significant portion of the organic content of the liquid organic waste that could otherwise be converted to energy products can be lost, depending on the type of front end processing and the type of organics in the material, before it gets to the anaerobic digestion system.

Commercial-scale composting is also subject to a variety of financial considerations including capital investment related to accommodating peak seasonal feedstock deliveries, compost process time, and controlling the timing of compost production to match the seasonal demand of the agricultural industry and other compost buyers. Further, the compost produced by these facilities is a low-value product, therefore municipalities have to pay to have the waste accepted.

SUMMARY

An exemplary system for converting solid and liquid organic waste materials comprises a biomixer, a first screening apparatus, a hydropulper, and a hydrocyclone. The biomixer is configured to convert a first portion of the solid organic waste materials, optionally mixed with a quantity of the liquid organic waste material as needed to obtain a proper moisture content, into a partially hydrolyzed biomass, and the first screening apparatus is configured to screen the partially hydrolyzed biomass into unders that pass through a screen mesh. The hydropulper is configured to receive the unders from the first screening apparatus and to create a slurry therefrom. A quantity of the liquid organic waste material can also be added to the hydropulper as a dilution agent to create the slurry. The hydrocyclone is configured to remove grit from the slurry. In some embodiments, the system further comprises a second screening apparatus, including a screen mesh, configured to screen a second portion of the organic waste materials into unders that pass through the screen mesh and overs that do not, wherein the hydropulper is configured to also receive the unders from the second screening apparatus. In some of these embodiments, a grinder is configured to grind the unders from the second screening apparatus, and the hydropulper is configured to receive the ground unders. The system can also comprise a sorting facility configured to remove undesirable materials from the organic waste materials. In some embodiments, the system further comprises an anaerobic digester configured to receive the slurry, and some of these embodiments further comprise a compost facility configured to receive residual solids from the anaerobic digester. In some embodiments, the liquid organic waste can also be added directly into the anaerobic digester with the slurry if the liquid organic waste is of a sufficient quality that pulping, grit removal, and the biomixer process are not necessary. For example, the liquid organic waste should be both free of grit and possess a small particle size of about 0.5 inches or less. The system can also comprise a liquid holding tank for holding received liquid organic waste material. The system can also comprise a liquid separator for separating the liquid organic waste material from received containers.

An exemplary method for converting organic waste materials comprises processing a first portion of the organic waste materials and a quantity of liquid organic waste material in a biomixer to create a partially hydrolyzed biomass, screening the partially hydrolyzed biomass into unders that pass through a first screen mesh, hydropulping the unders to remove heavier and lighter materials and to create a slurry of the remainder, and removing grit from the slurry. In some embodiments, the method further comprises screening a second portion of the organic waste materials into unders that pass through a second screen mesh and overs that do not pass through the second screen mesh. In these embodiments the unders from the second portion of the organic waste materials and a quantity of liquid organic waste materials are hydropulped with the unders from the partially hydrolyzed biomass to create the slurry. In further embodiments, the overs are processed in the biomixer with the first portion of the organic waste materials. In still other embodiments, the slurry and a quantity of liquid organic waste materials is anaerobically digested to produce biogas and a residual solid which can be dewatered and composted. In some instances, the water from dewatering the residual solid can be recycled back to hydropulping. In still further embodiments, the liquid organic waste materials are first separate from containers holding them and/ or stored in one or more holding tanks prior to the above processing.

DETAILED DESCRIPTION

Systems and methods are provided for converting solid and liquid organic waste materials from various municipal waste streams to useful products. These systems and methods are capable of receiving solid organic waste materials having a wide range of compositions such as, for example, yard waste, food waste, paper, and the organic fraction of municipal solid waste (MSW). The systems and methods convert the organic waste materials into a uniform biomass that is suitable for conversion to useful products, such as fuels. Through the steps of the various methods, the solid organic waste materials are progressively reduced in size and cleaned of contamination. Final sizing and cleaning is performed with a hydropulper and a hydrocyclone. A biomixer is advantageously provided, prior to the hydropulper, to partially hydrolyze organic waste materials that are not initially suitable for processing in the hydropulper. Anaerobic digestion of the resulting uniform material, can be employed, for instance, to convert the uniform biomass to biogas and a residual solid that is suitable for producing a high quality compost. Additionally, liquid organic waste materials can also be combined with the solid organic waste materials at several points in the process.

Figure 1:
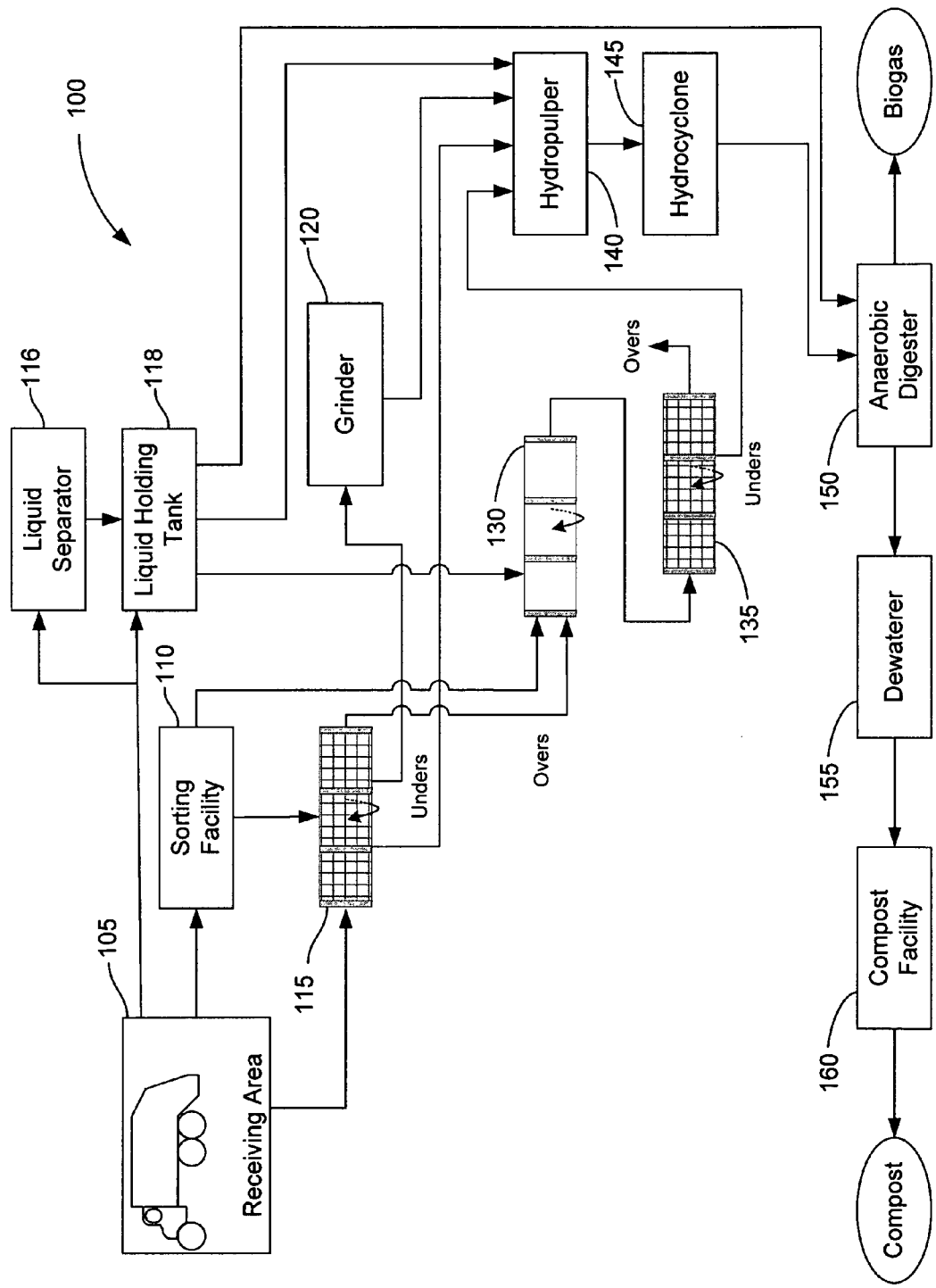
FIG. 1 is schematic representation of a system for the treatment of organic waste materials according to an embodiment of the present invention.

FIG. 1 provides a schematic representation of an exemplary system 100 for the treatment of organic waste materials. The system 100 is configured to receive and process organic waste materials into a uniform biomass that is a suitable feedstock for conversion to useful products. As discussed below, in some embodiments, the components of the system 100 are sited together as one facility, while in other embodiments the components are distributed across more than one facility and materials have to be transported between them, for example, by pipeline, truck, or rail.

The system 100 comprises a receiving area 105, such as a tipping floor, where the organic waste materials can be delivered to the system 100, for example, by municipal garbage trucks. In some embodiments, the organic waste materials are source separated before being brought to the facility 100, meaning that at the point of collection the organic waste materials have been segregated from non-organic waste materials. Source separated organic waste materials can comprise, for example, food waste, yard waste, paper, or any combination thereof, and can be derived from both residential and commercial sources. A source separated organic stream refers to the source separated organic materials of a common type that are collected from multiple sources.

An exemplary source separated food waste stream includes processed foods, vegetable matter, meat and dairy products, animal fat, vegetable oil, kitchen grease, and bones. An exemplary source separated yard waste stream includes branches, grass clippings, leaves, and other plant matter. An exemplary source separated paper stream includes newsprint, junk mail, paper and cardboard, some contaminated with food, fat, or kitchen grease, and organic paper associated with food preparation or consumption such as paper towels, paper plates, tissue, waxed paper, and waxed cardboard. Certain businesses can produce highly specific source separated organic streams such as sawdust and wood scraps from lumber yards and bread products from bakeries.

Thus, source separated organic waste materials can comprise a very specific type of waste material (e.g., food waste) or a diverse mixture of the various organic materials noted above. It is also noted that the composition of a source separated organic stream can vary over time. The composition of a source separated yard waste stream, for instance, will vary with the seasons and will include a larger fraction of lawn clippings during the Spring and Summer months. As will be described elsewhere herein, the system 100 is able to accommodate the compositional range of source separated organic streams.

As described below, decisions regarding how various organic waste materials of different compositions are to be handled by the system 100 can be made, for example, at the time the organic waste materials are received in the receiving area 105. Organic waste materials from various source separated organic streams can be commingled in the receiving area 105 before being further processed, or can be kept separated until later stages of the processing.

The system 100 comprises a sorting facility 110 where various unsuitable materials can be removed from the organic waste materials prior to further processing. The sorting facility 110 can comprise a sorting floor, a sorting line, or both, for example. Depending on the source of the organic waste materials, various degrees of sorting may be employed. A sorting floor is appropriate where little sorting is required, while a sorting line is useful for more significant sorting. For example, MSW is typically directed to the sorting line. On the other hand, some source separated organic waste streams may require a very limited amount of sorting, for instance, sawdust and wood debris collected from a lumber mill.

Unsuitable materials typically fall into three categories, hazardous waste, recyclable items, and problematic items. Hazardous waste includes materials that would otherwise contaminate the end product or pose worker safety problems and includes items such as batteries, pesticides, and paint. Recyclable items include such materials as glass, certain plastics, and certain metals. Problematic items are those items that are neither hazardous nor recyclable, but pose a danger of interfering with the operation of down-stream equipment. Examples of problematic items include rope, hose, plastic bags, clothing, buckets, and other large items. Hazardous waste can be directed to appropriate disposal, recyclable items can be directed to appropriate recycling facilities, and problematic items can be directed to reuse alternatives, where appropriate, or landfilling.

Figure 2:
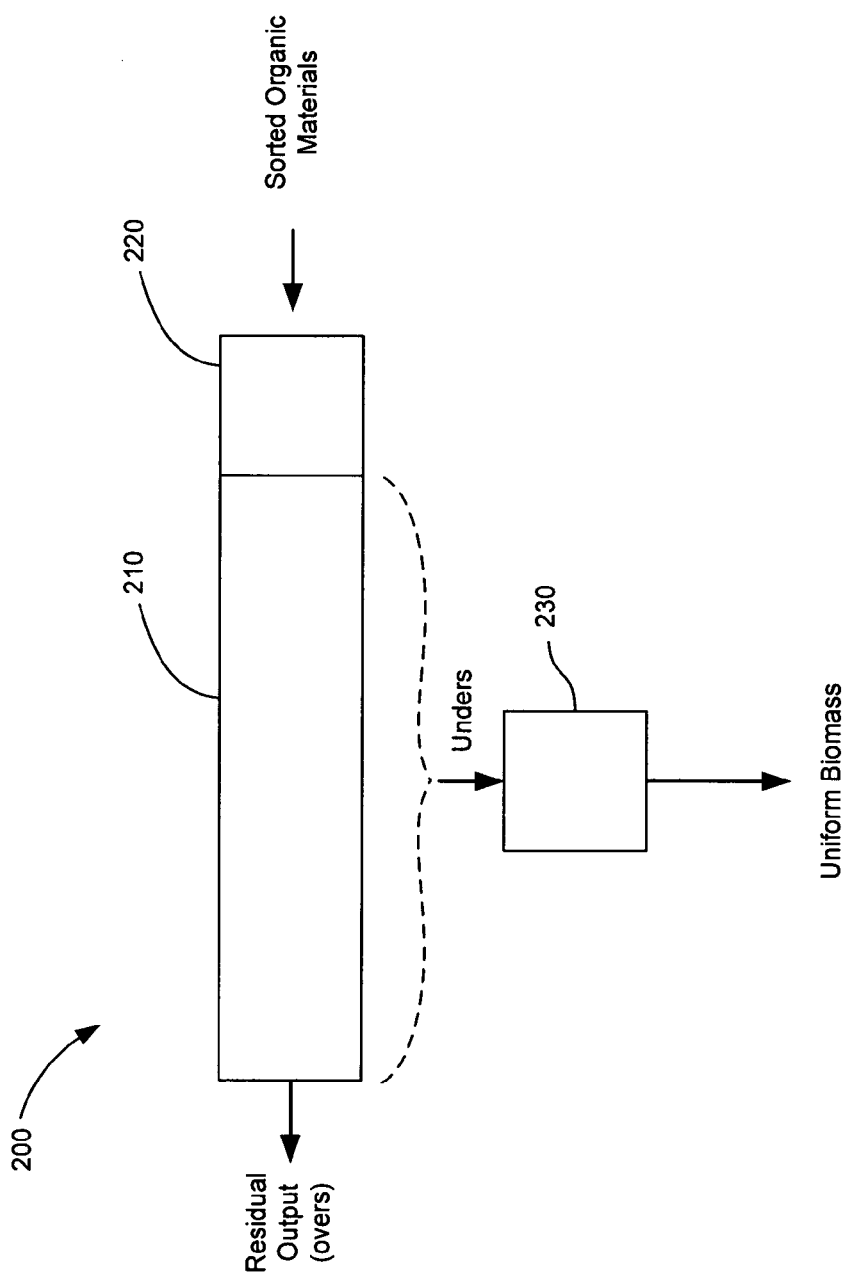
FIG. 2 is a schematic representation of a screening apparatus for use in the system of FIG. 1.

The system 100 further comprises a screening apparatus 115 that can include, for example, a trommel, a screening table, a perforated plate, a disc screen, a finger screen, or a shaker screen. The screening apparatus 115 is configured to screen the organic waste materials into a fraction of the smaller and more desirable "unders" that pass through a mesh of the screening apparatus 115 and a residual fraction of "overs" that do not pass through the screen mesh. As used herein, the terms "mesh" and "screen mesh" refer to the openings in the screening apparatus 115, which can be the square openings defined by a lattice of wires or the perforations of a perforated plate, for example. FIG. 2 shows a schematic representation of a screening apparatus 200 as described in U.S. application Ser. No. 10/954,550. The screening apparatus 200 comprises a screen 210 and an optional mixer 220. The screen 210 in the illustrated embodiment is a trommel. Mesh sizes for the screen 210 can be at least 1¼ inch, in the range from 2 to 12 inches, and in the range from 4 to 6 inches, in some embodiments. The mixer 220 can be used prior to the screen 210, where appropriate, to mix the organic waste materials. The mixer 220 serves to break open plastic bags, when present, and to break apart larger items such as melon rinds.

For some source separated organic waste streams, such as source separated food waste, the unders from the screening apparatus 115 will include the most organics-rich material, in other words, the material with the highest volatile solids content. The overs, on the other hand, will include more of the less desirable cellulostic material and plastics. Depending on the thoroughness of the sorting, the overs can also include unsuitable materials. In order to optimize the output of the screening apparatus 115, the mesh size of the screening apparatus 115 can be selected based on the composition of the organic waste materials and the desired quality of the unders. For a given organic waste stream, a smaller mesh size will increase the quality of the unders, but will also increase the amount of material in the residual fraction. Thus, the optimum mesh size for a given organic waste stream is the one that will pass the largest fraction of the organic waste stream without causing the unders to drop below a minimum quality threshold.

In some instances, the unders from the screening apparatus 115 are directed to a grinder 120, such as grinder 230 shown in FIG. 2. In FIG. 2, the unders are directed to the grinder 230 to be ground into a uniform biomass, while the overs can be directed to composting, landfilling, or further processing as described below. An exemplary grinder 230 is a vertical-feed hammer mill. Exemplary final particle size requirements for the uniform biomass produced by the grinder 230 specify a maximum particle size and allow for any size distribution below the maximum, for example, ¾ inch or less, ¼ inch or less, and 1/16 inch or less.

Figure 3:
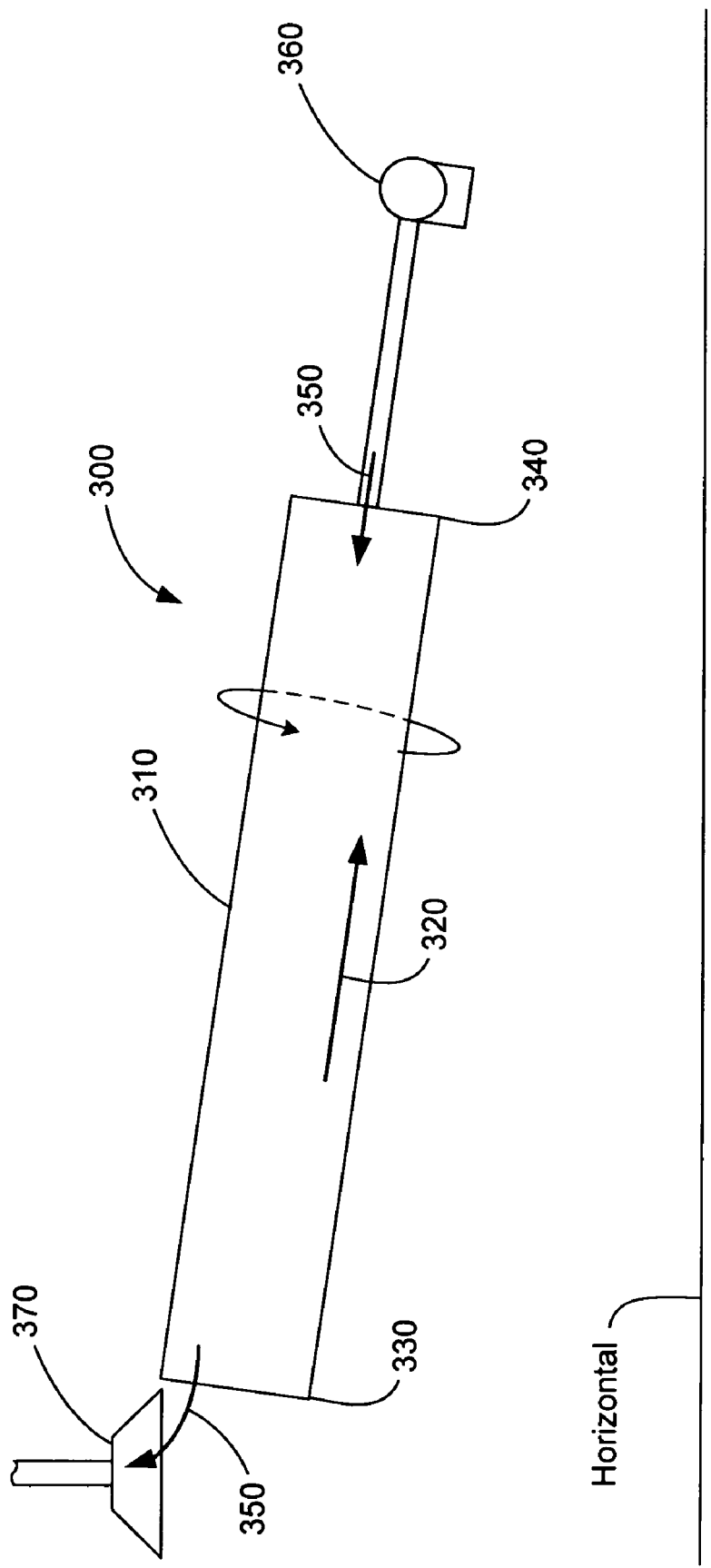
FIG. 3 is a schematic representation of a biomixer for use in the system of FIG. 1.

The system 100 also includes a biomixer 130. The biomixer 130 is a biomechanical device described in U.S. patent application Ser. No. 11/584,680. The biomixer 130 employs a combination of mechanical shearing and biological activity in a controlled environment to produce a partially hydrolyzed biomass. An exemplary biomixer 300 is shown in FIG. 3 and comprises a rotatable drum 310 that is sloped relative to the horizontal so that waste material (represented by arrow 320) introduced at a feed end 330 traverses the biomixer 300 to a discharge end 340. FIG. 3 also shows an air system for moving air (represented by arrows 350) through the biomixer 300 and, in some embodiments, for recirculating and/or recovering volatile fatty acids from the air 350. Components of the air system that are shown in FIG. 3 include an air injector 360, such as a blower, and an air collection device 370, such as a hood. Adjustments to the air flow through the drum 310 can be used to control the fermentation process therein. The air system can also be used to recover volatile fatty acids from the environment of the drum 310.

The drum 310 includes bacteria capable of facilitating a fermentation process. The bacteria can include any bacteria capable of facilitating a fermentation process, such as aerotolerant anaerobic bacteria. Aerotolerant anaerobic bacteria are specialized anaerobic bacteria characterized by a fermentative-type of metabolism. These bacteria live by fermentation alone, regardless of the presence of oxygen in their environment. Exemplary aerotolerant anaerobic bacteria include species in the genera *Desulfomonas, Butyrivibrio, Eubacterium, Lactobacillus, Clostridium*, and *Ruminococcus*.

In order to introduce the bacteria into the drum 310, the biological content of the organic waste materials can be adjusted, for instance, by addition of select bacteria prior to being loaded into the biomixer 300. The added bacteria can either be a cultured bacteria, or can be a bacteria that is recovered from a biomass previously produced by the biomixer 300. In the latter case, a small fraction of the biomass produced by the biomixer 300 is recirculated back into the organic waste materials being introduced into the biomixer 300. In some embodiments the small fraction of biomass added to the organic waste materials is ten percent or less of the mass of the incoming organic waste materials.

As shown in FIG. 1, the partially hydrolyzed biomass produced by the biomixer 130 is directed to a screening apparatus 135. The screening apparatus 135 can include a trommel or a screening table, for example. The screening apparatus 135 is configured to screen the partially hydrolyzed biomass into a fraction of unders that pass through a mesh of the screening apparatus 135 and a residual fraction of overs that do not pass through the screen mesh. Mesh sizes for the screen mesh can be at least 1¼ inch, in the range from 2 to 12 inches, and in the range from 4 to 6 inches, in some embodiments.

For some source separated organic waste streams, the unders from the screening apparatus 135 will include the most organics rich material, and the overs will include more of the less desirable cellulostic material and plastics. Depending on the thoroughness of the sorting, the overs can also include unsuitable materials. The mesh size of the screening apparatus 135 can be selected based on the composition of the organic waste materials and the desired quality of the unders in order to optimize the output of the screening apparatus 135. For a given organic waste stream, a smaller mesh size will increase the quality of the unders, but will also increase the amount of material in the residual fraction. Thus, the optimum mesh size for a given organic waste stream is the one that will pass the largest fraction of the organic waste stream without causing the unders to drop below a minimum quality threshold. As with the overs from the screening apparatus 115, the overs produced by the screening apparatus 135 can be directed to composting or a landfill.

The system 100 also comprises a hydropulper 140 including a vessel having an impeller. Exemplary hydropulpers are described in U.S. Pat. Nos. 5,377,917 and 6,379,505 both to Wiljan et al., both incorporated by reference herein. Organic waste materials are mixed with water in the vessel and agitated by the impeller. Through the addition of water, the solids content of the organic waste materials is reduced in the hydropulper 140 from a typical 25±7% solids content to an 8±2% solids content. Agitation by the impeller creates a slurry and tends to shear paper and plastic materials and otherwise causes a reduction in the particle size of the solids.

Within the hydropulper 140 the heavier materials such a glass, ceramics, stones, and metals tend to sink to the bottom, while lighter materials such as plastics float to the top. The lighter materials can be removed from the hydropulper 140, for example, be skimming the top of the slurry. The heavier materials can be periodically removed from the bottom of the hydropulper 140. The particle size of the solids can be controlled by withdrawing the slurry from a level beneath the level of the lighter fraction and screening the slurry to a typical half inch to one inch size, or less. The larger particles within the slurry that do not pass the screen can be recirculated for additional agitating.

In the manner described above, the hydropulper 140 produces a slurry with a uniform particle size that is transferred to a hydrocyclone 145. The hydrocyclone 145 is effective to remove grit from the slurry, as also described in U.S. Pat. No. 5,377,917. The resulting slurry, cleaned of grit, can be directed to an anaerobic digester 150. Anaerobic digestion by the anaerobic digester 150 produces biogas. The residual solids following anaerobic digestion can be dewatered by a dewaterer 155. The dewatered residual solids can then be composted at a compost facility 160. Hydrocyclones, anaerobic digesters, dewaterers, and compost facilities are all well known in the art.

In some embodiments, the system 100 includes a liquid holding tank 118 for holding received liquid organic waste material before the liquid organic waste material is passed to the biomixer 130, the hydropulper 140 and/or the anaerobic digester 150.

In some further embodiments, the system 100 includes a liquid separator 116 for removal of liquid organic waste material from received containers such as paper milk cartons, glass bottles, cans, plastic containers, etc. In these further embodiments, the separated liquid organic waste material is either passed to the liquid holding tank 118 or, alternatively (and not shown), passed directly to the biomixer 130, the hydropulper 140 and/or the anaerobic digester 150 by bypassing the liquid holding tank 118.

As noted above, in some embodiments the components of the system are located together in one facility, while in other embodiments the components are distributed across more than one facility. For example, the receiving area 105, the sorting facility 110, the screening apparatus 115 and 135, the grinder 120, and the biomixer 130, can be located in one facility at or near a solid waste transfer station while the hydropulper 140, hydrocyclone 145, anaerobic digester 150 and dewaterer 155 can be located at or near a waste water treatment facility. The compost facility 160 can be located at or near the anaerobic digester 150, or located at yet a third location. Similarly, the liquid separator 116 can be located at some other location with the resulting separated liquid organic waste delivered to the other components of the system 100.

Figure 4:
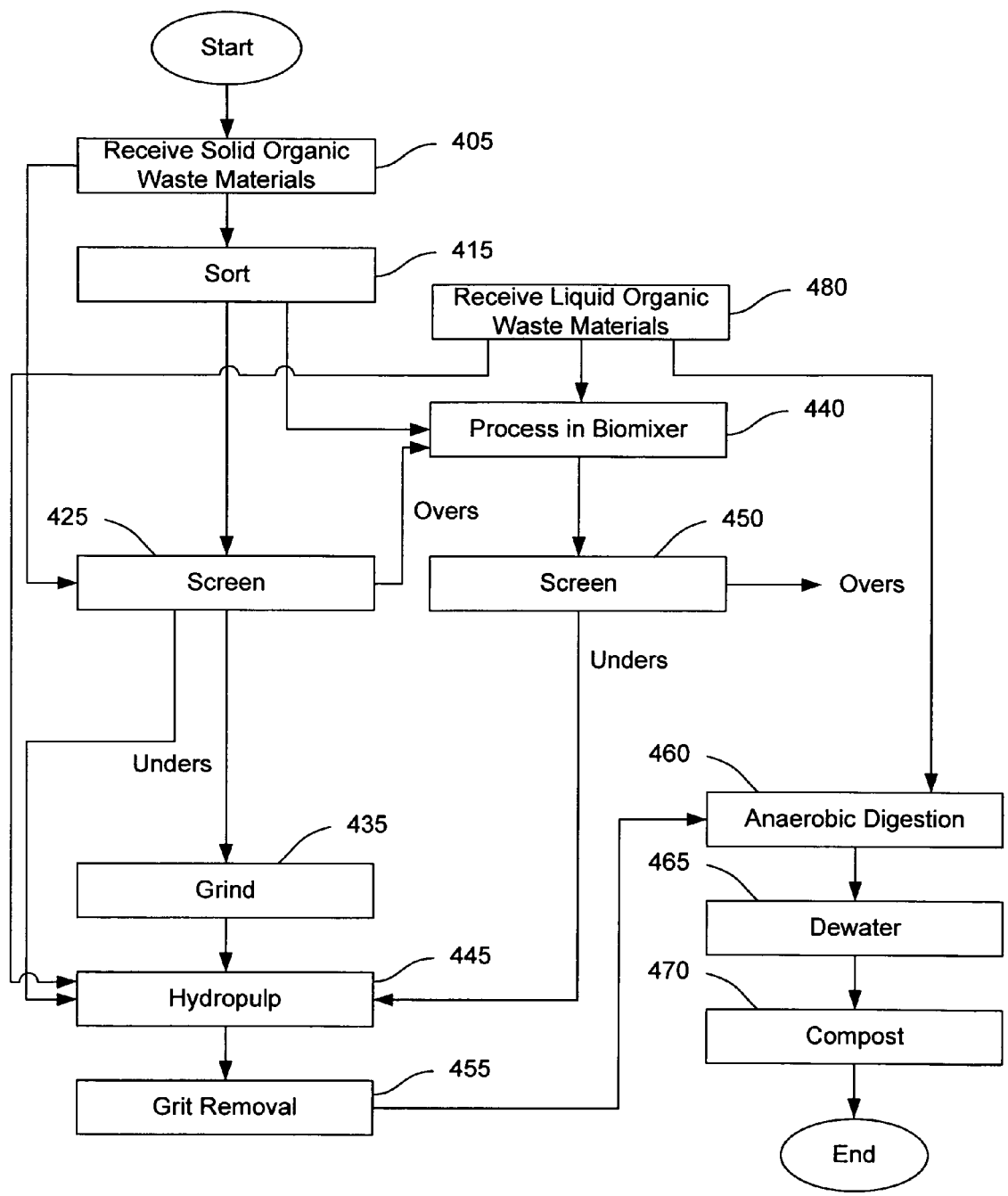
FIG. 4 is a flowchart representation of exemplary methods of the present invention.

FIG. 4 shows a flowchart representation pertaining to exemplary methods of processing organic waste materials through anaerobic digestion to produce biogas and a high quality compost. The various methods begin with receiving 405 solid organic waste materials. The solid organic waste materials are received 405 in the receiving area 105 (FIG. 1). In the receiving area 105 a decision is made regarding whether sorting 415 is required, which will depend on the nature of the received solid organic waste materials. Solid organic waste materials that do not need sorting 415 are directed to the screening apparatus 115 (FIG. 1), while those that do need sorting 415 are directed to the sorting facility 110 (FIG. 1).

Determining whether or not to sort 415 the solid organic waste materials, in some instances, relies on a visual inspection of the solid organic waste materials in the receiving area 105 to assess the presence of various unsuitable materials discussed above. If unsuitable materials are visible, the solid organic waste materials are directed to the sorting facility 110, otherwise, to the screening apparatus 115. In other instances the outcome of the decision is based on the type of solid organic waste materials without visual inspection. For example, MSW is always directed to the sorting facility 110. On the other hand, source separated food waste from reliable sources that is known to consistently have very low quantities of unsuitable materials can be directed to the screening apparatus 115 without visual inspection. It is noted that even if some unsuitable materials end up in the screening apparatus 115, the screening apparatus 115 will tend to screen those materials into the overs and out of the overall process.

Another factor to be assessed is whether the solid organic waste material includes a sufficient fraction of smaller particles that are suitable for immediate processing in the hydropulper 140 (FIG. 1). Such a fraction can be readily screened by the screening apparatus 115 to select that fraction. Materials that are suitable for immediate processing in the hydropulper 140 are those that will readily disintegrate in response to agitation in water to form a slurry. Source separated food waste ordinarily includes a sufficient fraction of such material. Source separated yard waste, on the other hand, typically does not include a sufficient fraction of smaller particles that are suitable for immediate processing in the hydropulper 140. These materials are directed, instead, to the biomixer 130 (FIG. 1) after sorting 415. In sum, a general rule is that sorting can be omitted when the solid organic waste materials include a sufficient fraction of smaller particles that are suitable for immediate processing in the hydropulper 140 and when the solid organic waste materials are deemed to not include unsuitable materials either by having passed a visual inspection or by virtue of being from a reliable source.

Solid organic waste materials that are deemed to require sorting are then sorted 415 at the sorting facility 110. The sorted solid organic waste materials are then directed to be screened 425 if the sorted solid organic waste materials include a sufficient fraction of smaller particles that are suitable for immediate processing in the hydropulper 140, otherwise the sorted solid organic waste materials are directed to the biomixer. Regardless of whether the sorted solid organic waste materials are screened 425 or sent to the biomixer 130, it should be noted that sorting 415 need not be exhaustive because in either pathway the solid organic waste materials will pass through a screening apparatus 115 or 135 that will tend to remove unsuitable materials. In particular, however, sorting 415 is intended to remove problematic materials that would interfere with the operation of the screening apparatus 115 or the biomixer 130. In the case of MSW, sorting 415 can also be used to remove recyclable materials.

If the sorted solid organic waste materials are to be screened 425, then the solid organic waste materials are directed to the screening apparatus 115. Following screening 425, the unders are directed to the hydropulper 140, and optionally to an intermediate step of grinding 435. Grinding 435 can be advantageous in that it reduces the dwell time in the hydropulper 140 that is necessary to create a slurry with a sufficiently small particle size. Reducing the dwell time in the hydropulper 140 improves the throughput of the hydropulper 140. The overs from screening 425 are preferably directed to the biomixer 130, but can alternatively be directed to the composting facility 160 or to a landfill.

As noted above, if the sorted solid organic waste materials are not directed to be screened 425, then the sorted solid organic waste materials are directed to be processed 440 in the biomixer 130. Processing 440 in the biomixer 130, as described above, takes organic materials that are not suitable for immediate processing in the hydropulper 140 and creates a partially hydrolyzed biomass that is suitable for hydropulping 445. Prior to hydropulping 445, the output of the biomixer 130 is first screened 450 to remove unsuitable materials that were not previously removed. These overs can be composted or directed to a landfill.

Hydropulping 445, for example with the hydropulper 140, agitates solid organic waste materials in water to create a slurry and to further separate out undesirable materials. The solid organic waste materials that are hydropulped 445 can be unders from screening 425, ground unders from grinding 435, or a partially hydrolyzed and screened biomass from processing 440 in the biomixer 130. The output from hydropulping 445 is directed to grit removal 455, for example, with the hydrocyclone 145 (FIG. 1). Grit removal 455 makes the slurry less abrasive, for instance, to pumps.

The slurry, following grit removal 455, is a very uniform biomass product that is a suitable feedstock for different processes. In the examples shown herein, the slurry is next directed to anaerobic digestion 460, but it will be appreciated that the slurry can be a feedstock for conversion to ethanol or other fuels through well known processes. In the case of anaerobic digestion 460, the resulting products are biogas and a residual solid. The residual solid can then be dewatered 465 and composted 470. The water that is removed can be recycled back into hydropulping 445 in those embodiments where the hydropulper 140, anaerobic digester 150, and dewaterer 155 are situated in close proximity to one another. Having been through a multi-step sizing and cleaning process, the dewatered residual solids from anaerobic digestion 460 are ideal for making a high quality compost.

It will be appreciated that the system 100 and the various processes outlined by FIG. 4 are highly adaptable. In some instances, for example, it may be more advantageous to direct some solid organic waste materials that would otherwise be suitable for hydropulping 445 instead to the biomixer 130 simply because extra capacity to receive that material exists in the biomixer 130 and those materials would otherwise have to wait for an extended period for the hydropulper 140. It will also be appreciated that different types of source separated waste materials can be commingled at various points. For instance, source separated paper waste, though typically directed out of the present system 100 for paper recycling, can be added as needed to the biomixer 130 to decrease the moisture content therein.

Further, the various processes outlined by FIG. 4 can be adapted to also handle liquid organic waste. In some exemplary methods, liquid organic waste can be received 480 independently of receiving 405 the solid organic waste materials. Examples of liquid organic waste materials that can be received 480 include blood waste from slaughterhouses, glycerin left over from biodeisel production, and various types of food waste such as spoiled or contaminated lots of milk, cheese whey, etc. Liquid organic waste from these types of sources can be advantageously uniform in terms of moisture content and composition.

In one embodiment, the liquid organic waste materials are separated from any containers such as paper milk cartons, glass bottles, cans, plastic containers, etc., prior to being added to the biomixer, the hydropulper and/or the anaerobic digester. Further, in some embodiments, the liquid organic waste materials, whether separated from any containers or simply received as liquid organic waste materials, are stored in one or more holding tanks prior to being added to the biomixer, the hydropulper and/or the anaerobic digester.

Various amounts of the liquid organic waste can be processed 440 in the biomixer, hydropulped 445, and/or anaerobically digested 460 directly, as illustrated in FIG. 4. Some of the liquid organic waste can be added to the biomixer to raise the moisture content to a desirable range, for example. Liquid organic waste can also be added to the hydropulper where the particle size of suspended solids is undesirably too large and/or the liquid organic waste includes unacceptably high levels of grit and/or other impurities. Where the liquid organic waste has a sufficiently small particle size and is suitably clean and free of grit, the liquid organic waste can be fed directly into the anaerobic digester.

In the foregoing specification, the present invention is described with reference to specific embodiments thereof, but those skilled in the art will recognize that the present invention is not limited thereto. Various features and aspects of the above-described present invention may be used individually or jointly. Further, the present invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A method for converting organic waste materials, comprising:
    processing a first portion of the organic waste materials and a quantity of liquid organic waste material in a biomixer to create a partially hydrolyzed biomass;
    screening the partially hydrolyzed biomass into unders that pass through a first screen mesh;
    hydropulping the unders to remove heavier and lighter materials and to create a slurry of the remainder; and
    removing grit from the slurry.

2. The method of claim 1 further comprising separating the quantity of liquid organic waste material from any containers prior to processing the first portion of the organic waste materials and the quantity of liquid organic waste material in the biomixer.

3. The method of claim 1 further comprising storing the quantity of liquid organic waste material in a holding tank prior to processing the first portion of the organic waste materials and the quantity of liquid organic waste material in the biomixer.

4. The method of claim 1 further comprising screening a second portion of the organic waste materials into unders that pass through a second screen mesh and overs that do not pass through the second screen mesh, wherein the unders from the second portion of the organic waste materials are hydropulped with the unders from the partially hydrolyzed biomass to create the slurry.

5. The method of claim 4 further comprising processing the overs with the first portion of the organic waste materials in the biomixer.

6. The method of claim 4 further comprising grinding the unders from the second portion of the organic waste materials prior to hydropulping.

7. The method of claim 1 further comprising sorting the organic waste materials prior to processing the first portion of the organic waste materials in the biomixer.

8. The method of claim 1 further comprising anaerobically digesting the slurry to produce biogas and a residual solid.

9. The method of claim 8 further comprising dewatering the residual solid and composting the dewatered residual solid.

10. The method of claim 9 further comprising recycling water from dewatering the residual solid back to hydropulping.

11. The method of claim 1 wherein the organic waste materials include source separated organic waste materials.

12. The method of claim 1 wherein the organic waste materials include municipal solid waste.

13. A method for converting organic waste materials, comprising:
  processing a first portion of the organic waste materials in a biomixer to create a partially hydrolyzed biomass;
  screening the partially hydrolyzed biomass into unders that pass through a first screen mesh;
  hydropulping the unders and a quantity of liquid organic waste material to remove heavier and lighter materials and to create a slurry of the remainder; and
  removing grit from the slurry.

14. The method of claim 13 further comprising separating the quantity of liquid organic waste material from any containers prior to hydropulping the unders and the quantity of liquid organic waste material.

15. The method of claim 13 further comprising storing the quantity of liquid organic waste material in a holding tank prior to hydropulping the unders and the quantity of liquid organic waste material.

16. The method of claim 13 further comprising screening a second portion of the organic waste materials into unders that pass through a second screen mesh and overs that do not pass through the second screen mesh, wherein the unders from the second portion of the organic waste materials are hydropulped with the unders from the partially hydrolyzed biomass to create the slurry.

17. The method of claim 16 further comprising processing the overs with the first portion of the organic waste materials in the biomixer.

18. The method of claim 16 further comprising grinding the unders from the second portion of the organic waste materials prior to hydropulping.

19. The method of claim 13 further comprising sorting the organic waste materials prior to processing the first portion of the organic waste materials in the biomixer.

20. The method of claim 13 further comprising anaerobically digesting the slurry to produce biogas and a residual solid.

21. The method of claim 20 further comprising dewatering the residual solid and composting the dewatered residual solid.

22. The method of claim 21 further comprising recycling water from dewatering the residual solid back to hydropulping.

23. The method of claim 13 wherein the organic waste materials include source separated organic waste materials.

24. The method of claim 13 wherein the organic waste materials include municipal solid waste.

25. A method for converting organic waste materials, comprising:
  processing a first portion of the organic waste materials in a biomixer to create a partially hydrolyzed biomass;
  screening the partially hydrolyzed biomass into unders that pass through a first screen mesh;
  hydropulping the unders to remove heavier and lighter materials and to create a slurry of the remainder;
  removing grit from the slurry; and
  anaerobically digesting the slurry and a quantity of liquid organic waste material to produce biogas and a residual solid.

26. The method of claim 25 further comprising separating the quantity of liquid organic waste material from any containers prior to anaerobically digesting the slurry and the quantity of liquid organic waste material.

27. The method of claim 25 further comprising storing the quantity of liquid organic waste material in a holding tank prior to anaerobically digesting the slurry and the quantity of liquid organic waste material.

28. The method of claim 25 further comprising screening a second portion of the organic waste materials into unders that pass through a second screen mesh and overs that do not pass through the second screen mesh, wherein the unders from the second portion of the organic waste materials are hydropulped with the unders from the partially hydrolyzed biomass to create the slurry.

29. The method of claim 28 further comprising processing the overs with the first portion of the organic waste materials in the biomixer.

30. The method of claim 28 further comprising grinding the unders from the second portion of the organic waste materials prior to hydropulping.

31. The method of claim 25 further comprising sorting the organic waste materials prior to processing the first portion of the organic waste materials in the biomixer.

32. The method of claim 25 further comprising dewatering the residual solid and composting the dewatered residual solid.

33. The method of claim 32 further comprising recycling water from dewatering the residual solid back to hydropulping.

34. The method of claim 25 wherein the organic waste materials include source separated organic waste materials.

35. The method of claim 25 wherein the organic waste materials include municipal solid waste.

* * * * *